United States Patent [19]

Takemoto et al.

[11] 4,071,511

[45] Jan. 31, 1978

[54] METHOD OF REMOVING FORMYL GROUPS FROM N-FORMYL-AMINO ACID AND N-FORMYL-PEPTIDE ESTERS HAVING FREE CARBOXYL GROUPS

[75] Inventors: Tadashi Takemoto, Toyonaka; Fusayoshi Kakizaki, Kawasaki; Yasuo Ariyoshi, Yokohama, all of Japan

[73] Assignee: Ajinomoto Co., Inc., Tokyo, Japan

[21] Appl. No.: 713,270

[22] Filed: Aug. 10, 1976

[30] Foreign Application Priority Data

Aug. 14, 1975 Japan .................................. 50-98817

[51] Int. Cl.² .......................................... C07C 103/52
[52] U.S. Cl. .............................. 260/112.5 R; 560/171
[58] Field of Search ...................... 260/112.5 R, 482 R

[56] References Cited

U.S. PATENT DOCUMENTS

| 3,933,781 | 1/1976 | Bachman et al. | 260/112.5 R |
|---|---|---|---|
| 4,021,418 | 5/1977 | Takemoto et al. | 260/112.5 R |

OTHER PUBLICATIONS

Sondheimer, et al; J. Am. Chem. Soc. 26, 1961, pp. 1847–1849.
Sheehan, et al; J. Am. Chem. Soc. 80, 1958, pp. 1154–1158.
Greenstein, et al; Chemistry of the Amino Acids 2, 1961, pp. 1246–1247, 1283–1284, 1294.

*Primary Examiner*—Delbert R. Phillips
*Attorney, Agent, or Firm*—Oblon, Fisher, Spivak, McClelland & Maier

[57] ABSTRACT

The masking N-formyl group of an N-formyl-amino acid ester or an N-formyl-peptide ester having a free carboxyl group is removed without major side reactions when the ester is contacted with a strong acid in a mixture of water and a specific organic solvent such as methyl ethyl ketone or acetonitrile. This method is specifically applicable to the production of L-aspartyl amino acid lower alkyl esters which are known as low calorie sweeteners.

9 Claims, No Drawings

METHOD OF REMOVING FORMYL GROUPS FROM N-FORMYL-AMINO ACID AND N-FORMYL-PEPTIDE ESTERS HAVING FREE CARBOXYL GROUPS

BACKGROUND OF THE INVENTION

1. Field of the Invention

This invention relates to the removal of masking formyl groups from amino acid and peptide esters having free carboxyl groups.

2. Description of the Prior Art

While the amino groups of amino acid and peptide esters having free carboxyl groups are readily masked by formyl groups, it was common practice heretofore instead to employ benzyloxycarbonyl and tert-butyloxycarbonyl groups for this purpose in the synthesis of peptides and similar reactions. These known masking groups require phosgene, a dangerously toxic gas, for their introduction, but they have the advantage of being removed easily when no longer required. No practical method of removing formyl groups from the nitrogen atoms of amino acid esters or peptide esters having free carboxyl groups was available prior to this invention.

SUMMARY OF THE INVENTION

Acid hydrolysis in water and/or methanol is the conventional method of removing formyl groups from amino groups and is effective, for example, in amino acids. This method, however, when applied to esters of amino acids or peptides having free carboxyl groups tends to remove the alcohol moiety from the ester or to esterify the free carboxyl group.

DETAILED DESCRIPTION OF THE PREFERRED EMBODIMENTS

It has now been found that formyl groups can be removed from the amino groups of amino acid esters and peptide esters having free carboxyl groups without major side reactions by contacting the esters with a strong acid in a mixture of water and a specific organic solvent. Therefore, the method of this invention is specifically applicable to the production of L-aspartyl amino acid esters such as α-L-aspartyl-L-phenylalanine lower alkyl esters and α-L-aspartyl-L-tyrosine lower alkyl esters which are known as low calorie sweeteners, from the corresponding N-formyl derivatives.

The strong acids useful in the method of this invention are acids having a first dissociation constant of not less than $1.0 \times 10^{-1}$ at 25° C. Such suitable acids include, but are not limited to, the conventional mineral acids such as hydrochloric and sulfuric acid. Strong organic acids such as benzenesulfonic acid, trifluoroacetic acid and monomethylsulfuric acid are equally effective, but do not offer any advantages that would justify their high cost.

The amino group that is to be stripped of a masking formyl group according to this invention may be that of any amino acid ester or peptide ester having a free carboxyl group moreover, and the result is not affected by many other reactive moieties in the ester, such as an amide or thiol group, or an amino group. The alcohol moiety of the ester has no significant bearing on the removal of the formyl group from the masked nitrogen atom. The esters of the lower alkanols having up to three carbon atoms and of benzyl alcohol are widely used in this art, and these alcohols provide typical although not necessary moieties for the esters which may serve as starting materials for the method of this invention. We are not aware of any amino acid or peptide ester, having a free carboxyl group, of a primary or secondary alcohol that cannot be successfully stripped of a masking formyl group by this method.

The specific organic solvents for use in this invention include monohydric alkanols having 3 or 4 carbon atoms, aliphatic ketones having 3 to 5 carbon atoms, acetonitrile, and a mixture of these solvents. Among these organic solvents, iso-propanol, sec-butanol, tert-butanol, acetone, methyl ethyl ketone and acetonitrile are preferred. Most preferable organic solvents are methyl ethyl ketone and acetonitrile. The preferred ratio of the amount of specific organic solvent to the amount of water depends on the kind of organic solvent used, but is easily determined by experiments. Water is usually used in a volume of 5 to 30% of that of the specific organic solvent. The mixed solvents employed in this invention may contain other organic solvents such as hydrocarbons (e.g., benzene, toluene), halogenated hydrocarbons (e.g., chloroform, ethylenedichloride), and ethers (e.g., tetrahydrofuran, dioxane). These other organic solvents may even improve the yield of the desired ester free from masking groups.

The reaction of this invention proceeds smoothly if the masked ester having a free carboxyl group and the strong acid are contacted with stirring in a mixture of water and the specific organic solvent. Temperature affects the reaction rate in the usual manner. The temperature of said mixture is usually between 20° and 80° C during said contacting operation. If an optically active product is desired, the highest temperature which will not cause significant racemization is preferred in order to achieve a short reaction time. The maximum yield is obtained at 70° C in 1 to 3 hours in most instances, while 4 to 10 hours may be needed at 50° C and 1 to 3 days at about 25° C.

The amount of strong acid used is not critical, but the use of a large amount tends to remove the alcohol moiety from the ester and/or to break the peptide bond, if any. The strong acid is usually used in an amount of from 0.5 to 4 moles per mole of the formyl groups in the ester. The strong acid is added to the reaction mixture at any time during the reaction. The entire amount of acid may be used at the beginning of reaction, but it is also possible to gradually add the acid to the reaction mixture during the progress of the reaction.

Unless the reaction mixture is employed directly in a subsequent reaction, the amino acid ester or peptide ester having free carboxyl groups which is free from masking formyl groups may be recovered by methods conventional in themselves. These include lowering the temperature of the mixture, adding solvents non-miscible with the medium, partial evaporation of the medium, and the like.

The following Examples are further illustrative of this invention.

EXAMPLE 1

3.2 g of N-formyl-α-L-aspartyl-L-phenylalanine methyl ester and 3 ml of 4N-hydrochloric acid were added to a mixture of 60 ml of tert-butanol and 5 ml of water, and the solution was stirred at 65° C for 10 hours.

An aliquot of the reaction mixture was diluted and analyzed by an amino acid autoanalyzer. It was found to contain α-L-aspartyl-L-phenylalanine methyl ester in a yield of 70% based on the starting ester.

EXAMPLES 2 TO 8

The procedure similar to that of Example 1 was repeated at 50° C under the conditions shown in Table 1 wherein the results are also summarized.

EXAMPLES 9 AND 10

The procedure similar to that of Example 1 was repeated at 50° C under the conditions shown in Table 2, except that 3.52 g of N-formyl-α-L-aspartyl-L-tyrosine ethyl ester was used instead of the N-formyl α-L-aspartyl-L-phenylalanine methyl ester.

The results are summarized in Table 2.

EXAMPLE 11

14.3 g of N-formyl-L-aspartic anhydride (0.1 mole) was added to a mixture of 100 ml of methyl ethyl ketone and 24.0 g of acetic acid (0.4 mole). The solution was stirred at room temperature for 15 minutes. A solution of 17.9 g of L-phenylalanine methyl ester (0.1 mole) dissolved in 200 ml of methyl ethyl ketone was added to the above solution and stirred at room temperature for 6 hours to produce N-formyl-α-L-aspartyl-L-phenylalanine methyl ester.

In accordance with the method of this invention, the reaction mixture was added to 300 ml of methyl ethyl ketone, 50 ml of water and 30 ml of 4N-hydrochloric acid and stirred at 50° C for 10 hours to remove the formyl group.

The reaction mixture was added to 100 ml of water. The pH was adjusted to 2.0 with sodium carbonate. The methyl ethyl ketone layer was separated from the water layer and washed twice with 100 ml of water. The water layer and washings were combined and concentrated under reduced pressure. The residue was added to 30.5 ml of conc. hydrochloric acid and water until the total volume became 135 ml. The solution was stored overnight in a refrigerator to precipitate crystals of α-L-aspartyl-L-phenylalanine methyl ester hydrochloride. The crystals were filtered and weighed 17.5 g.

The crystals were dissolved in 130 ml of water. After the pH of the solution was adjusted to 4.8 it was stored overnight in a refrigerator. It yielded a precipitate of 12.4 g of free α-L-aspartyl-L-phenylalanine methyl ester (41% 20 based on the starting N-formyl-L-aspartic anhydride).

$[\alpha]_D^{20} = +31.7°$ (C=1, acetic acid)

The precipitate was identified as pure α-L-aspartyl-L-phenylalanine methyl ester by an amino acid autoanalyzer.

EXAMPLE 12

The procedure similar to that of Example 11 was repeated, the same volume of acetonitrile being used instead of methyl ethyl ketone throughout.

12.6 g of free, pure α-L-aspartyl-L-phenylalanine methyl ester was obtained (42% yield based on the starting N-formyl-L-aspartic anhydride).

$[\alpha]_D^{20} = +31.6°$ (C=1, acetic acid)

Table 1

| Example No. | Solvent (ml) | 4N-hydrochloric acid ml | Reaction acid hour | Yield % |
|---|---|---|---|---|
| 2 | acetonitrile (30) + water (5) | 3 | 8 | 73 |
| 3 | acetonitrile (60) + water (5) | 3 | 10 | 76 |
| 4 | methyl ethyl ketone (30) + water (5) | 3 | 8 | 69 |
| 5 | methyl ethyl ketone (60) + water (5) | 3 | 10 | 73 |
| 6 | acetone (30) + water (5) | 3 | 8 | 66 |
| 7 | iso-propanol (20) + benzene (10) + water (5) | 3 | 8 | 65 |
| 8 | sec-butanol (30) + water (5) | 3 | 8 | 63 |
| Control 1 | water (35) | 3 | 8 | 49 |
| Control 2 | methanol (30) + water (5) | 3 | 8 | 54 |

Table 2

| Example No. | Solvent ml | 4N-hydrochloric acid ml | Reaction time hour | Yield % |
|---|---|---|---|---|
| 9 | acetonitrile (60) + water (5) | 3 | 10 | 74 |
| 10 | methyl ethyl ketone (60) + water (5) | 3 | 10 | 73 |

What is claimed as new and desired to be secured by Letters Patent of the United States is:

1. A method of removing the formyl group from the nitrogen atom of an N-formyl-amino acid ester or N-formyl-peptide ester having a free carboxyl group which comprises contacting said ester with a strong acid in a mixture of water and a specific organic solvent, said strong acid having a first dissociation constant of not less than $1.0 \times 10^{-1}$ at 25° C, said specific organic solvent being selected from the group consisting of monohydric alkanols having 3 or 4 carbon atoms, aliphatic ketones having 3 to 5 carbon atoms and acetonitrile, and said water being used in a volume of from 5 to 30% of that of said specific organic solvent.

2. The method of claim 1, wherein said strong acid is hydrochloric acid or sulfuric acid, and is used in an amount of from 0.5 to 4 moles per mole of the formyl groups in said ester.

3. The method of claim 1, wherein said organic solvent is selected from the group consisting of iso-propanol, sec-butanol, tert-butanol, acetone, methyl ethyl ketone, and acetonitrile.

4. The method of claim 1, wherein said organic solvent is methyl ethyl ketone or acetonitrile.

5. The method of claim 1, wherein the alcohol moiety of said ester is an alkyl group having up to three carbon atoms or benzyl.

6. The method of claim 1, wherein said ester is an ester of a primary or secondary alcohol.

7. The method of claim 4, wherein said ester is α-L-aspartyl-L-phenylalanine lower alkyl ester or α-L-aspartyl-L-tyrosine lower alkyl ester, said lower alkyl group having up to three carbon atoms.

8. The method of claim 1, wherein the temperature of said mixture is between 20° and 80° C during said contacting operation.

9. The method of claim 1, which further comprises recovering the resulting deformylated amino acid ester or peptide ester having a free carboxyl group.

* * * * *